1

United States Patent [19]

Kamishima

[11] Patent Number: 4,655,741
[45] Date of Patent: Apr. 7, 1987

[54] BLOOD COMPONENT RESTORATION APPARATUS

[75] Inventor: Hideo Kamishima, Tokyo, Japan

[73] Assignee: Takeo Jyuji, Matsudo, Japan

[21] Appl. No.: 770,300

[22] Filed: Aug. 27, 1985

[51] Int. Cl.⁴ .............................................. A61M 5/00
[52] U.S. Cl. ........................................ 604/6; 604/283;
604/414; 604/408; 604/410; 604/411; 604/412
[58] Field of Search ............... 604/283, 5, 6, 408–414,
604/905, 262; 285/3, 401, 402

[56] References Cited

U.S. PATENT DOCUMENTS

| | | | |
|---|---|---|---|
| 3,625,212 | 12/1971 | Rosenberg et al. | 604/6 |
| 3,805,794 | 4/1974 | Schlesinger | 604/283 |
| 4,150,673 | 4/1979 | Watt | 604/408 |
| 4,161,949 | 7/1979 | Thanawalla | 604/905 |
| 4,256,106 | 3/1981 | Shoor | 604/905 |
| 4,271,865 | 6/1981 | Galloway et al. | 285/401 |
| 4,338,933 | 7/1982 | Bayard et al. | 604/905 |
| 4,433,973 | 2/1984 | Kurtz et al. | 604/905 |
| 4,508,367 | 4/1985 | Oreopoulos et al. | 285/3 |
| 4,511,359 | 4/1985 | Vaillancourt | 604/905 |

Primary Examiner—C. Fred Rosenbaum
Assistant Examiner—Sherri E. Vinyard
Attorney, Agent, or Firm—Felfe & Lynch

[57] ABSTRACT

A blood component restoration apparatus comprises: an exsanguinating needle; an exsanguinating tube and a blood component supplying tube both of which are connected to the exsanguinating needle in parallel with each other; an exsanguinating bag which is connected to the exsanguinating tube and is provided with a blood component discharging pipe; a first connecting member which is mounted on a front end of the blood component discharging pipe and is provided with a guide hole in its end surface, which guide hole extends in an axial direction of the first connecting member; and a second connecting member which is mounted on a front end of the blood component supplying tube and is provided with a guide pin in its end surface, which guide pin is inserted into the guide hole of the first connecting member.

2 Claims, 10 Drawing Figures

FIG. I
PRIOR ART

BLOOD COMPONENT RESTORATION APPARATUS

BACKGROUND OF THE INVENTION

1. Field of the Invention:

The present invention relates to a blood component restoration apparatus with the use of which blood exsanguinated from a blood donor is subjected to an operation of separating only a blood component necessary for a blood recipient from the blood, while the other blood components not necessary for the blood recipient are restored to the blood donor.

2. Description of the Prior Art:

At first, with reference to FIGS. 1 to 3, a typical example of a conventional restoration apparatus for blood components will be hereinbelow described, with the use of a conventional restoration apparatus, blood exsanguinated from the blood donor is subjected to an operation of separating only blood plasma from the blood, while the other blood components are restored to the blood donor.

In the drawings, 1 designates an exsanguinating needle, 2 designates an exsanguinating bag provided with a blood component discharging pipe 3 in its upper portion. The bag 2 is made of flexible synthetic resin films piled up and fused in their peripheries with each other to form a bag. The exsanguinating bag 2 is connected with the exsanguinating needle 1 through an exsanguinating tube 4. 5 designates a blood plasma receiving bag made of transparent resin films as is in the case of the exsanguinating bag 2, which is connected with the exsanguinating bag 2 through a blood plasma supplying tube 6.

7 designates a filtering/mixing unit constructed of a filtering tank portion 9 and a mixing tank portion 10, in which filtering tank portion 9 a net 8 is received, and the mixing tank portion 10 is provided under the filtering tank portion 9 to be communicated with the same portion 9. An upper portion of the unit 7 are provided with a blood component supplying tube 13 and a physiological saline solution transfusing tube 18. On a front end 11 of the blood component supplying tube 13 is mounted a blood component transfusing needle 12 which is connected to the blood component discharging pipe 3 provided in the upper portion of the exsanguinating bag 2. On a front end 14 of the physiological saline solution transfusing tube 18 is mounted a physiological saline solution transfusing needle 17 which is connected to a physiological saline solution vessel 16 in which the physiological saline solution 15 has been received, which vessel 16 will be described later. In a lower portion of the filtering/mixing unit 7 is provided with a mixed liquid transfusing tube 21, which mixed liquid is prepared by mixing the blood components and the physiological saline solution 15, and an end portion 19 of a mixed liquid transfusing tube 21 is connected to the exsanguinating tube 4 through a branched pipe 20 provided on a midway of the exsanguinating tube 4.

Now, a blood restoring operation performed by such restoration apparatus will be hereinbelow described. As shown in FIG. 1, exsanguinating operation of the blood is performed by stabbing the exsanguinating needle 1 into the blood donor's vein to exsanguinate the blood 23 which is supplied to the exsanguinating bag 2 through the exsanguinating tube 4. When a prescribed amount of the blood is exsanguinated, the exsanguinating tube 4 is closed at its portion between the branched pipe 20 and the exsanguinating bag 2 to the extent of a certain length thereof and then cut at the thus closed portion thereof. After that, the exsanguinating bag 2 containing the blood 23 is treated by means of a centrifugal separator while connected with a blood plasma bag 5 through a blood plasma supplying tube 6, so that a blood plasma 24, which is one of the components of the blood 23 with a specific gravity smaller than any of the other components of the blood 23, floats on the top of the other components 25 of the blood 23 to be separated therefrom as shown in FIG. 2, which other blood components 25 comprise red blood corpuscle, white blood corpuscle and blood platelet and are not required to be supplied to the blood recipient. Next, only the thus floated and separated blood plasma 24 is forcibly supplied to the blood plasma receiving bag 5 through the blood plasma supplying tube 6 under the effect of pressure developed in the exsanguinating bag 2. After that, the blood plasma supplying tube 6 is closed at its portion between the exsanguinating bag 2 and the blood plasma receiving bag 5 to the extent of a certain length thereof and cut at the thus closed portion thereof.

As shown in FIG. 3, then, the exsanguinating bag 2 containing the other blood components 25 is inverted so that to the blood component discharging pipe 3, which is now directed downward, is connected to the blood component transfusing needle 12 by forcibly inserting the needle 12 into the pipe 3. Whereby the other blood components 25 are supplied to the filtering tank portion 9 of the filtering/mixing unit 7 through the blood component supplying tube 13, while the physiological saline solution transfusing needle 17 is forcibly inserted into the vessel 16 so that the physiological saline solution 15 contained in the vessel 16 is also supplied to the filtering tank portion 9 of the filtering/mixing unit 7 through the physiological saline solution transfusing tube 18. The other blood components 25 having passed through the filtering tank portion 9 which contains a net 8 in its interior is mixed with the physiological saline solution 15 in the mixing tank portion 10 of the filtering/mixing unit 7 to prevent the other blood components 25 from coagulating so that the resultant mixed liquid is tarnsfused back into the vein of the blood donor 22. As described above, the other blood components 25, which are the remainder of the blood 23 from which the blood plasma 24 has been separated, are restored to the blood donor 22. Thereafter, all the used exsanguinating bag 2, blood component discharging pipe 3, exsanguinating tube 4 and blood plasma receiving bag 5 are discarded and in their place are installed new ones 2, 3, 4 and 5, respectively to make it possible that another new exsanguinating/restoring operation to be conducted.

In the above-mentioned blood exsanguinating/restoring operation, since there is only one blood donor and all the processes of the blood exsanguinating, centrifugal separating and restoring are sequentially conducted, it is possible to surely restore the other blood components 25, which are not transfused to the blood recipient, to the blood donor. On the other hand, for example, as is in a group exsanguinating operation, in case that a large number of the blood donors are subjected to the exsanguinating operation to provide a large number of exsanguinating bags in each of which has been received the blood exsanguinated from each individual blood donor, which exsanguinating bags are simultaneously subjected to the centrifugal separating process. And then the thus separated blood components, which are precipitated and are not required by the blood recipient, are restored to the individual blood donor, the following problem occurs. Namely, since the exsanguinating tube 4 connecting the exsanguinating needle 1 with the exsanguinating bag 2 is cut off before the centrifugal separating process of the thus exsanguinated blood is conducted, it is necessary to write each individual blood donor's name and his blood type on a front surface of each of the exsanguinating bags 2 in the exsanguinating operation in order to make it possible to surely identify later each of the exsanguinating bags 2 as each individual blood donor's by referring his name and blood type written on the front surface of his exsanguinating bag 2, whereby the other blood components 25 of each individual blood donor 22 can be surely restored to the same blood donor 22 in the blood restoring operation in which the blood component transfusing needle 12 is forcibly inserted into the blood component discharging pipe 3 of the exsanguinating bag 2. However, these writing and referring operations of the blood donor's name and his blood type are cumbersome and therefore constitute defects inherent in the conventional blood component restoration apparatus, in which there is further a fear that, in case that there are a plurality of the blood donors whose names and blood types are identical with each other, the blood components of one blood donor could be restored to another blood donor by mistake unless the identification operation of each individual blood donor is performed under stringent measures. This constitutes a further another defect inherent in the conventional restoration apparatus.

SUMMARY OF THE INVENTION

It is an object of the present invention to provide a blood component restoration apparatus which eliminates the above defects inherent in the conventional blood component restoration apparatus, i.e., eliminates a necessity for writing each individual blood donor's name and blood type on each of the exsanguinating bags and another necessity for identifying each of the exsanguinating bags as each individual blood donor's, and further easily eliminates the fear that the blood components of one blood donor is restored to another blood donor by mistake.

The above object of the present invention is accomplished by providing a blood component restoration apparatus comprising: an exsanguinating needle; an exsanguinating tube and a blood component supplying tube both of which are connected to the exsanguinating needle in parallel with each other; an exsanguinating bag which is connected to the exsanguinating tube and is provided with a blood component discharging pipe; a first connecting member mounted on a front end of the blood component discharging tube; and a second connecting member mounted on a front end of the blood component supplying tube, so that first and second connecting members can be opposed to each other. In one of the thus opposed end surfaces of the first and second connecting members is provided a guide pin extending in an axial direction of the first and second connecting members while in the other of the opposed end surfaces is provided a guide hole in which the guide pin is inserted.

In an embodiment of the blood component restoration appparatus of the present invention, one of the first and the second connecting members is provided a pipe-like portion while the other one of the first and the second connecting members is provided a sleevelike portion which is inserted into the pipe-like portion. In an inner peripheral surface of the pipe-like portion there is further provided a guide groove or a guide projection both of which extend in an axial direction of the pipe-like portion, while in an outer peripheral surface of the sleeve-like portion there is further provided a guide projection or a guide groove which projection or which groove is brought into a slidable contact with the guide groove or the guide projection of the pipe-like portion in an insertion manner, so that a misconnecting operation of the connecting members between different couples of the connecting members is more surely prevented from occurring so as to guarantee a sure restorating operation of the blood components to be conducted.

As further another embodiment of the present invention, a needle member is provided in a front end opening portion of the blood component supplying tube in the first connecting member, while in a front end of the blood component discharging tube in the second connecting member there is provided a virgin film which could be pierced with the above needle member when the second connecting member is connected with the first connecting member.

DESCRIPTION OF THE PREFERRED EMBODIMENT

Figure 1:
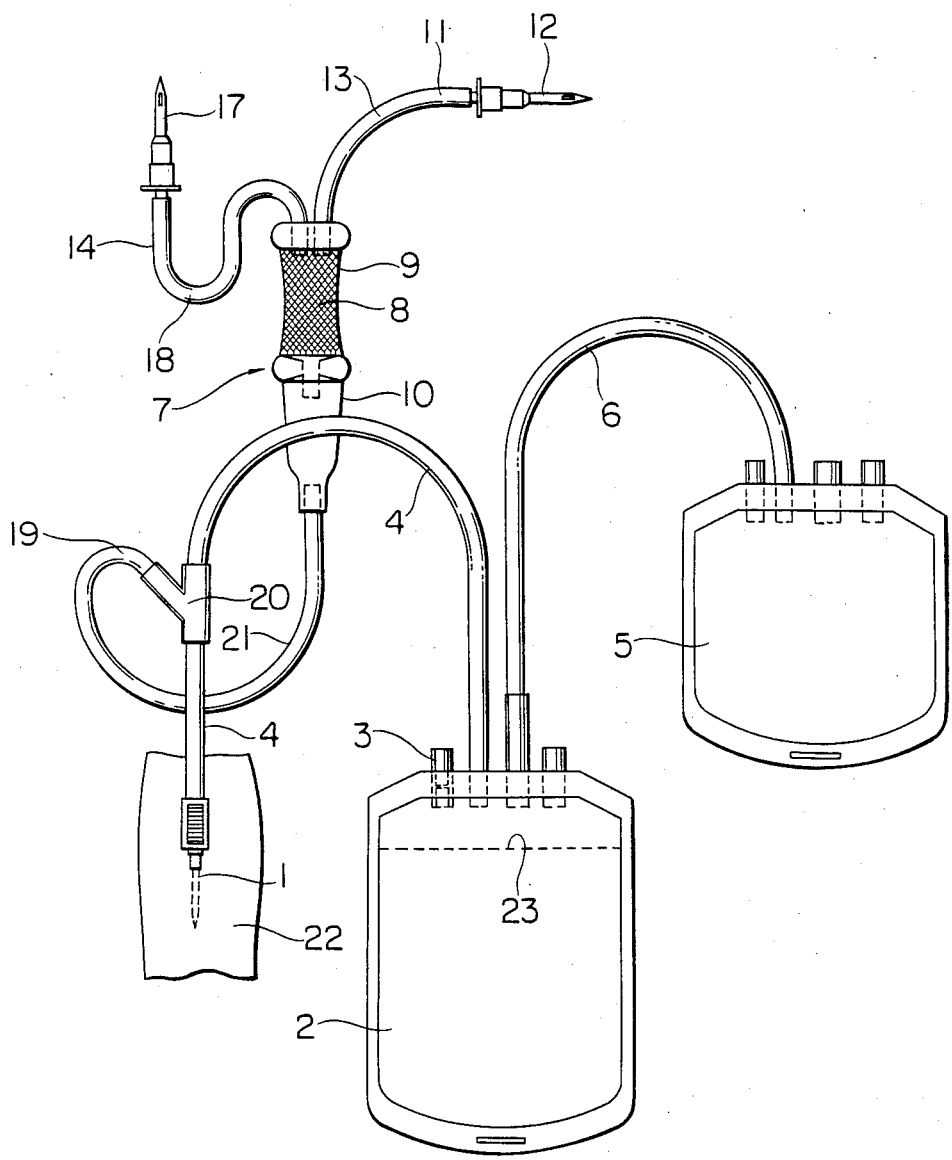
FIG. 1 is a front view of a typical conventional blood component restoration apparatus in a blood exsanguinating operation.

In the embodiment of the blood component restoration apparatus of the present invention shown in FIGS. 4 to 10, most of the parts thereof have the same constructions as those of the conventional blood component restoration apparatus, therefore such most parts of the present invention are designated by the same reference numerals as those used in the above description of the conventional restoration apparatus and description of such most parts of the restoration apparatus of the present invention will be hereinbelow omitted. And the remaining parts of the restoration apparatus of the present invention, which are different from those of the conventional restoration apparatus, will be mainly described hereinbelow.

Figure 4:
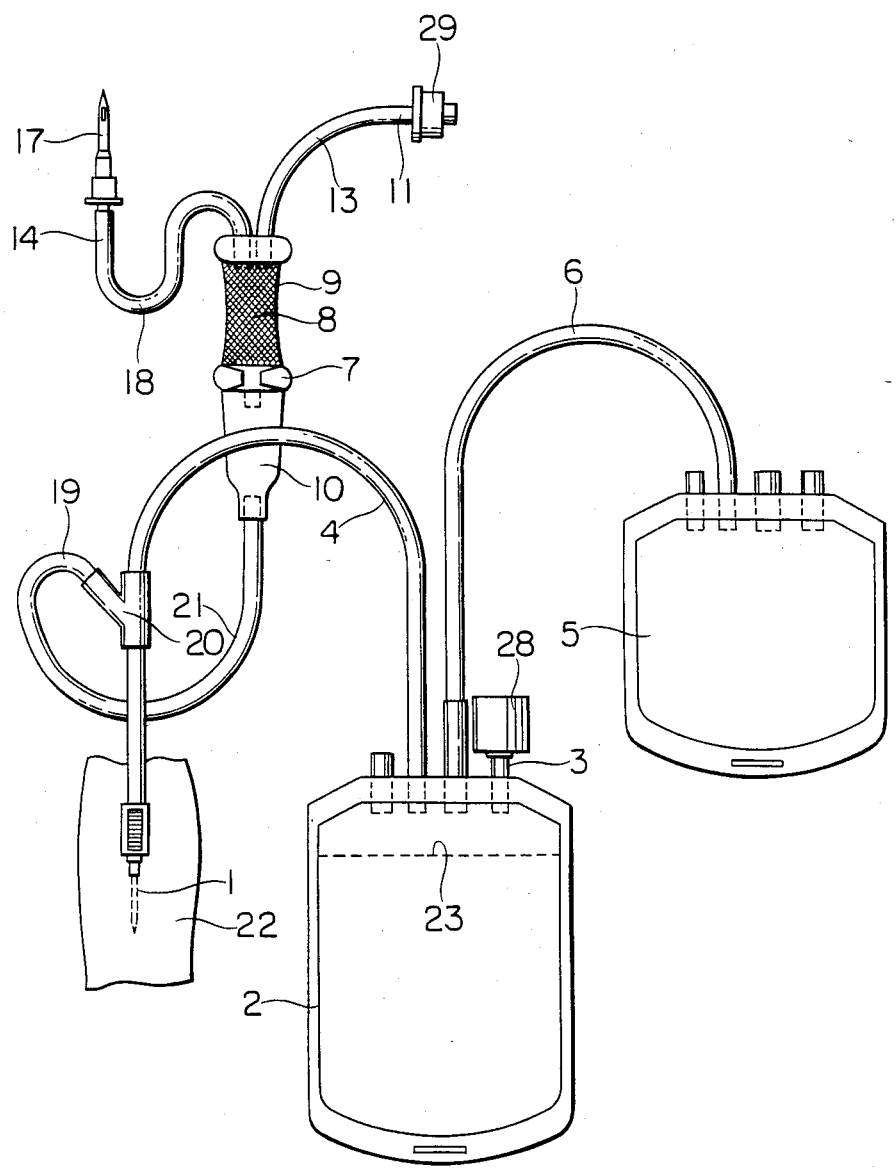
FIG. 4 is a front view of an embodiment of a blood component restoration apparatus of the present invention in an exsanguinating operation.

With reference to FIG. 4, the embodiment of the present invention is different from the conventional restoration apparatus in that the embodiment of the present invention is provided with a first connecting member 28 and a second connecting member 29 in a one, free or front end of each of the blood component discharging tube 3 and blood component supplying tube 13, respectively.

Figure 5:
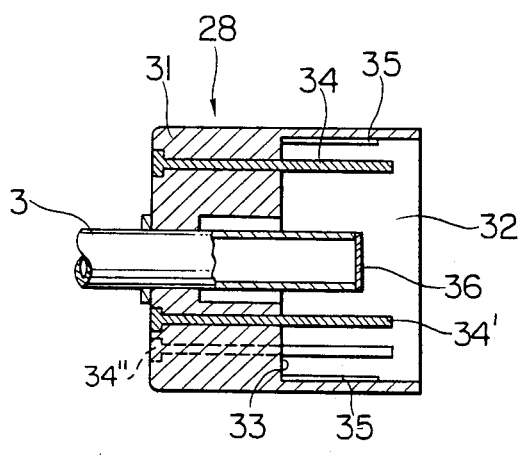
FIG. 5 is a partially longitudinal sectional front view of the first connecting member of the restoration apparatus shown in FIG. 4.
Figure 6:
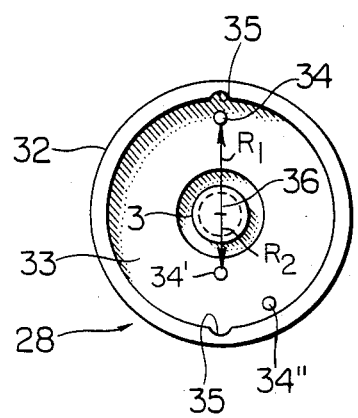
FIG. 6 is a right side view of the first connecting member shown in FIG. 5.

The details of the first connecting member 28 are shown in FIGS. 5 and 6. A pipe-like portion 32 is formed in one side of a main body 31 of the first connecting member 28. On a bottom wall or end surface 33 of which pipe-like portion 32 are provided at least two guide pins 34, 34', 34" projecting from the end surface at different radial distances $R_1$, $R_2$ from the center thereof, further on an inner peripheral surface of which pipe-like portion 32 are provided a plurality of guide grooves 35 extending in an axial direction of the pipe-like portion 32. In a central portion of the main body 31 of the first connecting member 28 is inserted the blood component discharging pipe 3 a front end of which is placed in the pipe-like portion 32 and is provided with a virgin film 36 closing an opening of the front end of the blood component discharging pipe 3.

Figure 7:
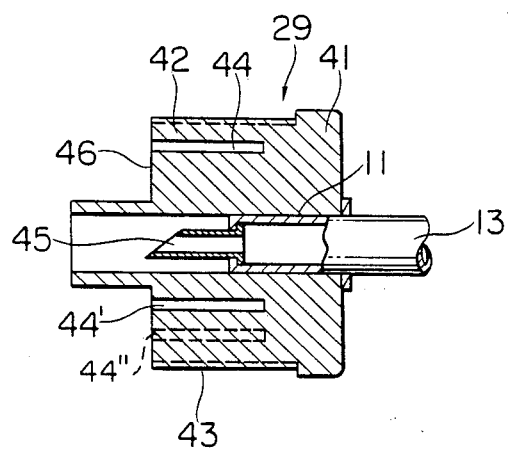
FIG. 7 is a partially longitudinal sectional front view of the second connecting member of the restoration apparatus shown in FIG. 4.
Figure 8:
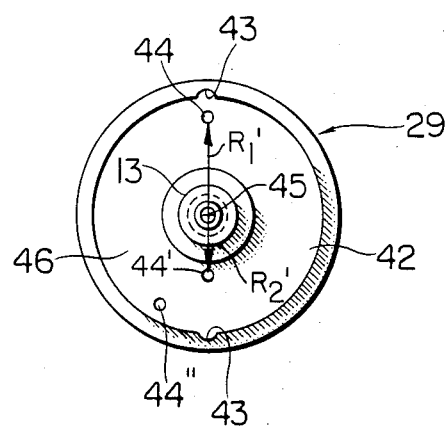
FIG. 8 is a left side view of the second connecting member shown in FIG. 7.

The details of the second connecting member 29 are shown in FIGS. 7 and 8. A sleeve-like portion 42 is provided in a sleeve-like main body 41 of the second connecting member 29, the sleeve-like portion 42 is inserted in the pipe-like portion 32 of the first connecting member 28. On an outer peripheral surface of which sleeve-like portion 42 is provided a plurality of guide projections 43 each of which is inserted in the guide groove 35 of the first connecting member 28. And on an end surface 46 of which main body 41 are provided at least two guide holes 44, 44', 44" at least two of which are at different radial distances $R_1'$, $R_2''$ from the center of the end surface 46 thereof for receiving the guide pins 34, 34' of the first connecting member 28. The end surface 46 is opposite to the bottom wall surface 33 of the first connecting member 28. In a central portion of the main body 41 of the second connecting member 29 is inserted the blood component supplying tube 13 in a front end 11 of which is provided a connecting pipe 45.

In these first and second connecting members 28 and 29, it is possible to provide the guide pins 34 and the guide holes 44 or to provide the guide grooves 35 and the guide porjections 43, respectively. By selecting the guide pins 34 and the guide holes 44 or by selecting the guide grooves 35 and the guide projections 43 in shape, length, position and number, it is ensured that the specified connecting members are connected with each other and therefore prevent them from being connected with other connecting members.

Figure 2:
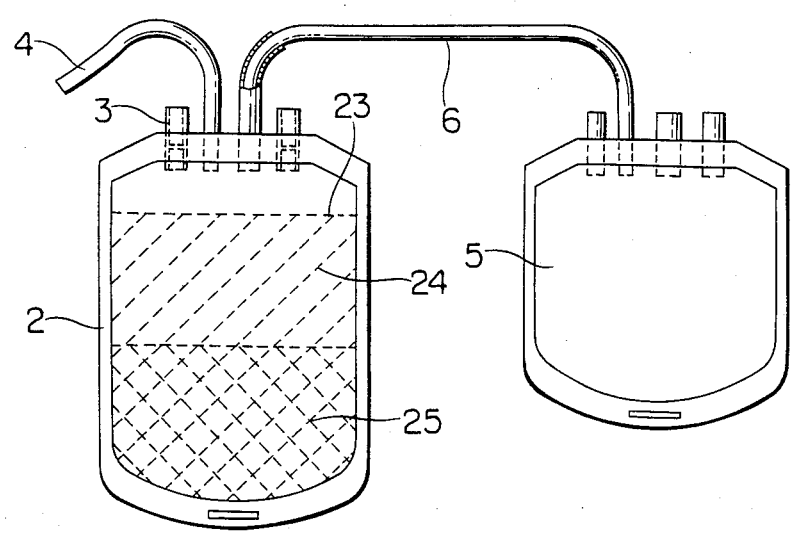
FIG. 2 is a partial front view of the conventional blood component restoration apparatus shown in FIG. 1, in which the blood exsanguinated by the restoration apparatus is separated into light blood component and heavy blood components.

In use, the exsanguinating operation is performed in the same manner as shown in FIG. 1 and the blood component separating operation is performed in the same manner as shown in FIG. 2, both of which operations are the sames as those performed in the conventional apparatus.

Figure 3:
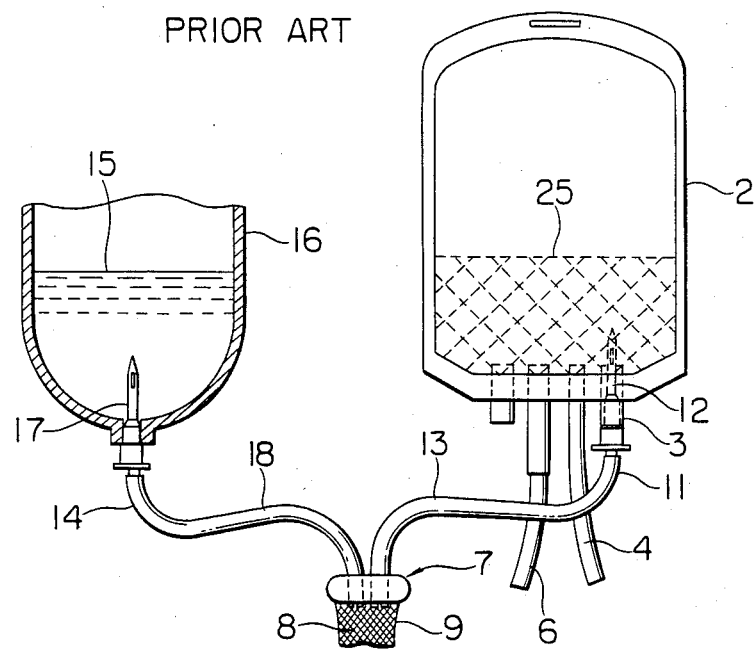
FIG. 3 is a partial front view of the conventional restoration apparatus shown in FIG. 1, in a blood restoring operation.
Figure 9:
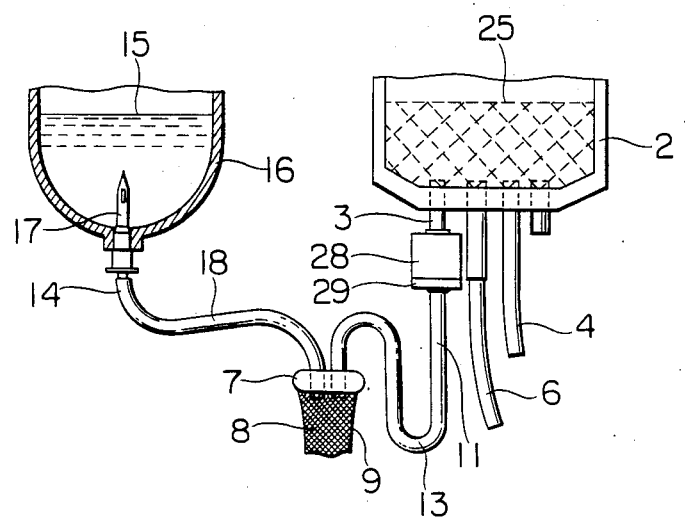
FIG. 9 is a partial front view of the blood component restoration apparatus shown in FIG. 4, in the blood component restoring operation.
Figure 10:
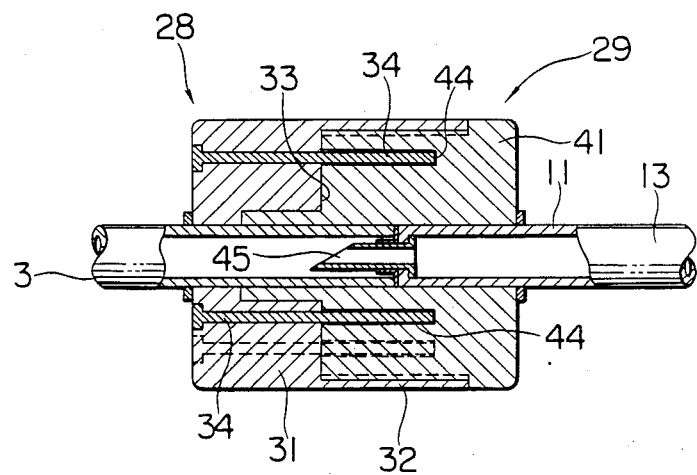
FIG. 10 is a partially longitudinal sectional front view of the connecting portion of the restoration apparatus shown in FIG. 9.

After these operations, the blood component restoring operation is performed as shown in FIGS. 9 and 10 in accordance with the present invention. Before starting the restoring operation, the connecting members 28 and 29 are connected with each other as shown in FIG. 10. In this connecting operation of the connecting members 28 and 29, the sleeve-like portion 42 of the connecting member 29 is inserted into the pipe-like portion 32 of the connecting member 28 while the guide projections 43 and the guide pins 34 are inserted into the guide grooves 34 and the guide holes 44 respectively so that the virgin film 36 is pierced by the front end of the connecting pipe 45, whereby the connecting members 28 and 29 are completely integrally connected with each other. Consequently, through this integral connection of the connecting members 28 and 29, it is possible to perform the blood component restoring operation similar to that performed in the conventional restoration apparatus shown in FIG. 3.

In the blood component restoring operation with the use of the restoration apparatus of the present invention, it is absolutely impossible to connect a connecting member of one specified couple of the connecting members with a connecting member of another specified couple of the connecting members, while the connecting members of the same specified couple are connectable only with each other, since the connecting members 28 and 29 constitute as individual specified couples different from other couples of the connecting members 28 and 29 in entire configuration due to the differences of the shape, size and arrangement of the parts. Consequently, even when a large number of the blood donors are subjected to the exsanguinating operation at one time resulting in a large number of the exsanguinating bags in which the thus obtained blood is contained are produced to be simultaneously subjected to the centrifugal separating operation of the blood component, it is not required to write each individual blood donor's name and blood type in each of the exsanguinating bags for identifying his own exsanguinating bag later, according to the present invention. This makes it possible to eliminate the cumbersomeness in writing the blood donor's name and blood type on the exsanguinating bag and referring them later for identifying his exsanguinating bag, which cumbersomeness is inherent in the conventional restoration apparatus, and ensures that the blood donor's own blood components are restored to him.

The present invention has been described in detail sufficient to enable one of ordinary skill in the art to make and use. It is believed that certain modifications and alterations of the preferred embodiments of the present invention will occur to others upon reading and understanding of the specification, and it is intended to include all such alterations and modifications as a part of the present invention, insofar as they come within the scope of the appended claims.

What is claimed is:

1. A blood component restoration apparatus comprising:
    an exsanguinating needle;
    an exsanguinating tube and a blood component supplying tube, each connected at one end to said exsanguinating needle;
    a blood component discharging tube;
    an exsanguinating bag connected to the other end of said exsanguinating tube and connected to one end of said blood component discharging tube; and
    first and second connecting members respectively on the other, front end of said blood component discharging tube and the other, front end of said blood component supplying tube, said first and said second connecting members thereby being able to be opposed to each other, each of said first and second connecting members having an end surface with at least two guide pins in one of the thus-opposed end surfaces of said first and said second connecting members, said guide pins then extending in an axial direction of said first and said second connecting members, and at least two guide holes in the other of said opposed end surfaces for receiving respective ones of said guide pins, said guide pins and guide holes being located at different radial distances from the centers of said end surfaces therewith, one of said first and second connecting members having a pipe-like portion and the other one of said members having a sleeve-like portion for insertion within the inner peripheral surface of said pipe-like portion, one of said inner peripheral surface of said pipe-like portion and said sleeve-like portion having one of at least one guide groove and at least one guide projection and the other of said portions having the other for slidable contact with each other when said sleeve-like portion is inserted within said inner peripheral surface of said pipe-like portion, the guide groove and guide projection extending in the axial direction of the portions therewith.

2. The blood component restoration apparatus as set forth in claim 1, wherein:

a needle member is provided in a front end opening portion of said blood component supplying tube in said first connecting member, while in a front end of said blood component discharging tube in said second connecting member is provided a virgin film which is pierced with said needle member when said second connecting member is connected with said first connecting member.

* * * * *